(12) United States Patent
Birk

(10) Patent No.: US 9,173,757 B2
(45) Date of Patent: Nov. 3, 2015

(54) APPARATUS AND METHOD FOR REMOTE DEFLATION OF INTRAGASTRIC BALLOON

(75) Inventor: Janel A. Birk, Oxnard, CA (US)

(73) Assignee: APOLLO ENDOSURGERY, INC., Austin, TX (US)

( * ) Notice: Subject to any disclaimer, the term of this patent is extended or adjusted under 35 U.S.C. 154(b) by 359 days.

(21) Appl. No.: 12/698,906

(22) Filed: Feb. 2, 2010

(65) Prior Publication Data

US 2010/0174307 A1 Jul. 8, 2010

Related U.S. Application Data

(63) Continuation-in-part of application No. 11/735,194, filed on Apr. 13, 2007, now abandoned.

(51) Int. Cl.
*A61M 29/00* (2006.01)
*A61F 2/04* (2013.01)
*A61F 5/00* (2006.01)

(52) U.S. Cl.
CPC .................. *A61F 5/003* (2013.01); *A61F 5/004* (2013.01); *A61F 2210/0014* (2013.01)

(58) Field of Classification Search
CPC ..... A61F 5/0003; A61F 5/0013; A61F 5/003; A61F 5/0036; A61F 5/004; A61F 5/0043; A61F 5/0046
USPC .................. 606/192, 195; 623/23.65, 23.67; 604/93.01, 95.05, 99.01, 99.02
See application file for complete search history.

(56) References Cited

U.S. PATENT DOCUMENTS

| | | |
|---|---|---|
| 1,702,974 A | 2/1929 | MacDonald |
| 2,163,048 A | 6/1939 | McKee |
| 3,667,081 A | 6/1972 | Burger |
| 3,719,973 A | 3/1973 | Bell |
| 3,840,018 A | 10/1974 | Heifetz |
| 3,919,724 A | 11/1975 | Sanders et al. |
| 4,118,805 A | 10/1978 | Reimels |
| 4,430,392 A | 2/1984 | Kelley et al. |
| 4,485,805 A | 12/1984 | Foster, Jr. |
| 4,545,367 A | 10/1985 | Tucci |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Patient Information Brochure, "Living With the Bib/BioEnterics Intragastric Balloon Program," Inamed Health, May 1, 2005, 1-10 pp.

(Continued)

*Primary Examiner* — Katherine Rodjom
(74) *Attorney, Agent, or Firm* — Gordon & Jacobson, PC

(57) ABSTRACT

An intragastric balloon system for facilitating weight loss in a human or animal patient generally includes a flexible shell suitable for placement in a digestive track of a patient and capable of being inflated with a fluid. The system further includes a valve mechanism coupled to the shell, an actuator for opening the valve mechanism to effect release of fluid from the shell, and a remote control device capable of sending a signal from outside the patient to the actuator in order to effectuate deflation of the shell in vivo and without surgical intervention.

15 Claims, 10 Drawing Sheets

(56) References Cited

U.S. PATENT DOCUMENTS

| | | | |
|---|---|---|---|
| 4,592,355 A | 6/1986 | Antebi | |
| 4,598,699 A | 7/1986 | Garren et al. | |
| 4,607,618 A | 8/1986 | Angelchik | |
| 4,636,213 A | 1/1987 | Pakiam | |
| 4,694,827 A | 9/1987 | Weiner et al. | |
| 4,723,547 A | 2/1988 | Kullas et al. | |
| 4,881,939 A | 11/1989 | Newman | |
| 4,930,535 A | 6/1990 | Rinehold | |
| 4,969,899 A | 11/1990 | Cox, Jr. | |
| 5,074,868 A | 12/1991 | Kuzmak | |
| 5,084,061 A | 1/1992 | Gau et al. | |
| 5,211,371 A | 5/1993 | Coffee | |
| 5,226,429 A | 7/1993 | Kuzmak | |
| 5,289,817 A | 3/1994 | Williams et al. | |
| 5,449,368 A | 9/1995 | Kuzmak | |
| 5,527,340 A | 6/1996 | Vogel | |
| 5,601,604 A | 2/1997 | Vincent | |
| 5,658,298 A | 8/1997 | Vincent et al. | |
| 5,693,014 A | 12/1997 | Abele et al. | |
| 5,725,507 A | 3/1998 | Petrick | |
| 5,748,200 A | 5/1998 | Funahashi | |
| 5,819,749 A | 10/1998 | Lee et al. | |
| RE36,176 E | 3/1999 | Kuzmak | |
| 5,938,669 A | 8/1999 | Klaiber et al. | |
| 6,074,341 A | 6/2000 | Anderson et al. | |
| 6,102,678 A | 8/2000 | Peclat | |
| 6,102,897 A * | 8/2000 | Lang | 604/246 |
| 6,102,922 A | 8/2000 | Jakobsson et al. | |
| 6,152,922 A | 11/2000 | Ouchi | |
| 6,290,575 B1 | 9/2001 | Shipp | |
| 6,454,699 B1 | 9/2002 | Forsell | |
| 6,454,785 B2 | 9/2002 | DeHoyos Garza | |
| 6,464,628 B1 | 10/2002 | Forsell | |
| 6,470,892 B1 | 10/2002 | Forsell | |
| 6,503,264 B1 | 1/2003 | Birk | |
| 6,511,490 B2 | 1/2003 | Robert | |
| 6,547,801 B1 | 4/2003 | Dargent et al. | |
| 6,579,301 B1 | 6/2003 | Bales et al. | |
| 6,629,776 B2 | 10/2003 | Bell et al. | |
| 6,733,512 B2 * | 5/2004 | McGhan | 606/192 |
| 6,733,513 B2 | 5/2004 | Boyle et al. | |
| 6,746,460 B2 | 6/2004 | Gannoe et al. | |
| 6,840,257 B2 | 1/2005 | Dario et al. | |
| 6,994,095 B2 | 2/2006 | Burnett | |
| 7,020,531 B1 | 3/2006 | Colliou et al. | |
| 7,037,344 B2 | 5/2006 | Kagan et al. | |
| 7,056,305 B2 | 6/2006 | Garza Alvarez | |
| 7,214,233 B2 | 5/2007 | Gannoe | |
| 2002/0095181 A1 | 7/2002 | Beyar | |
| 2002/0139208 A1 | 10/2002 | Yatskov | |
| 2002/0183782 A1 | 12/2002 | Tsugita et al. | |
| 2003/0073880 A1 | 4/2003 | Polsky et al. | |
| 2003/0106761 A1 | 6/2003 | Taylor | |
| 2005/0055039 A1 | 3/2005 | Burnett et al. | |
| 2005/0131485 A1 | 6/2005 | Knudson et al. | |
| 2005/0190070 A1 | 9/2005 | Rudduck et al. | |
| 2005/0192615 A1 | 9/2005 | Torre et al. | |
| 2005/0240279 A1 | 10/2005 | Kagan et al. | |
| 2005/0250979 A1 * | 11/2005 | Coe | 600/31 |
| 2005/0261711 A1 | 11/2005 | Okada et al. | |
| 2005/0267595 A1 | 12/2005 | Chen et al. | |
| 2005/0267596 A1 | 12/2005 | Chen | |
| 2006/0020278 A1 | 1/2006 | Burnett et al. | |
| 2006/0025799 A1 | 2/2006 | Basu | |
| 2006/0069403 A1 * | 3/2006 | Shalon et al. | 606/192 |
| 2006/0142700 A1 | 6/2006 | Sobelman | |
| 2006/0229702 A1 | 10/2006 | Agnew | |
| 2007/0016262 A1 | 1/2007 | Gross | |
| 2007/0083224 A1 | 4/2007 | Hively | |
| 2007/0135829 A1 | 6/2007 | Paganon | |
| 2007/0147170 A1 * | 6/2007 | Hood et al. | 366/127 |
| 2007/0156248 A1 | 7/2007 | Marco | |
| 2007/0173881 A1 | 7/2007 | Birk et al. | |
| 2007/0288033 A1 | 12/2007 | Murature et al. | |
| 2008/0172079 A1 | 7/2008 | Birk | |
| 2008/0208240 A1 | 8/2008 | Paz | |
| 2008/0243071 A1 | 10/2008 | Quijano et al. | |
| 2008/0255601 A1 | 10/2008 | Birk | |
| 2009/0131968 A1 | 5/2009 | Birk | |
| 2009/0259246 A1 | 10/2009 | Eskaros et al. | |
| 2010/0087843 A1 | 4/2010 | Bertolote et al. | |
| 2010/0100079 A1 | 4/2010 | Berckan et al. | |
| 2010/0168783 A1 | 7/2010 | Murature et al. | |
| 2010/0174307 A1 | 7/2010 | Birk | |
| 2010/0274194 A1 | 10/2010 | Sobelman et al. | |

FOREIGN PATENT DOCUMENTS

| | | |
|---|---|---|
| DE | 88 04 765 U1 | 5/1989 |
| DE | 102007025312 | 11/2008 |
| EP | 1396242 | 3/2004 |
| EP | 1396243 | 3/2004 |
| EP | 1774929 | 4/2007 |
| EP | 2095798 | 9/2009 |
| FR | 2797181 | 2/2001 |
| FR | 2823663 | 10/2002 |
| FR | 2852821 | 10/2004 |
| FR | 2855744 | 12/2004 |
| FR | 2941617 | 8/2010 |
| GB | 2086792 | 5/1982 |
| JP | 63-279854 | 11/1988 |
| JP | 1049572 | 2/1989 |
| JP | 63-264078 | 10/1998 |
| WO | WO 00/15158 | 3/2000 |
| WO | WO 01/10359 | 2/2001 |
| WO | WO 01/49245 | 7/2001 |
| WO | WO 01/66166 | 9/2001 |
| WO | WO 02/35980 | 5/2002 |
| WO | WO 03/055419 | 7/2003 |
| WO | WO 03/105732 | 12/2003 |
| WO | WO 2004/019671 | 3/2004 |
| WO | WO 2005/007231 | 1/2005 |
| WO | WO 2006/020370 | 6/2006 |
| WO | WO 2006/063593 | 6/2006 |
| WO | WO 2006/090018 | 8/2006 |
| WO | WO 2006/118744 | 11/2006 |
| WO | WO 2007/011086 | 10/2007 |
| WO | WO 2010/042062 | 4/2010 |

OTHER PUBLICATIONS

Bib Data Sheet Directions for Use, "BioEnterics Intragastric Balloon System," Inamed Health, 1-12 pp.

Bib Bioenterics Intragastric Balloon Program, "Taking the Next Step/Take Control of Your Weight and Your Life," Inamed Health, Apr. 29, 2004, 1-9 pp.

Bib Bioenterics Intragastric Balloon Program, "Take Control of Your Weight and Your Life/the Solution for You," Inamed Health, Jan. 19, 2004, 1-2 pp.

S.A. Xanthakos, "Bariatric surgery for extreme adolescent obesity: Indications, outcomes, and physiologic effects on the gut-brain axis", Elsevier Pathophysiology 15, 2008, pp. 135-146.

Baggio et al. "Biology of Integrins: GLP-1 and GIP"; Gastroenrology; V. 132; pp. 2131-2157; 2007.

Berne et al.; "Physiology"; V. 5; pp. 55-57, 210, 428 540, 579, 584, 591; 2004.

Boulant et al.; "Cholecystokinin in Transient Lower Oesophageal Sphincter Relation Due to Gastric Distension in Humans"; Gut; V. 40; pp. 575-581; 1997.

Bradjewin et al.; "Dose Ranging Study of the Effects of Cholecystokinin in Healthy Volunteers"; J. Psychiatr. Neurosci.; V. 16 (2); pp. 91-95; 1991.

Chaudri, Owais; "Can Gut Hormones Control Appetite and Prevent Obesity?" Diabetes Care, V. 31, Supp. 2, Feb. 2008.

Cohen et al.; "Oxyntomodulin Suppresses Appetite and Reduces Food in Humans"; J. Clin. Endocrinol. Metab.; V. 88; pp. 4696-4701; 2003.

Dakin et al.; "Oxyntomodulin Inhibits Food Intake in the Rat"; Endocrinology; V. 142; pp. 4244-4250; 2001.

Dakin et al.; "Peripheral Oxyntomodulin Reduces Food Intake and Body Weight gain in Rats" Endocrinology; V. 145; pp. 2687-2695; 2004.

(56) References Cited

OTHER PUBLICATIONS

Davison, J.; "Activation of Vagal-Gastric Mechanoreceptors by Cholecystokinin"; Proc. West. Pharmocol. Soc.; V. 29; pp. 363-366; 1986.

Ekblad et al.; "Distribution of Pancreatic Peptide and Peptide-YY"; Peptides; V. 23; pp. 251-261; 2002.

Greenough et al.; "Untangling the Effects of Hunger, Anxiety and Nausea on Energy Intake During Intravenous Cholecystokinin Octapeptide (CCK-8) Infusion" Physiology and Behavior; V. 65 (2); pp. 303-310, 1998.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Houpt; "Gastrointestinal Factors in Hunger and Satiety"; Neurosci. and Behav. Rev.; V. 6; pp. 145-164; 1982.

Kissileff et al.; "Peptides that Regulate Food Intake: Cholecystokinin and Stomach Distension Combine to Reduce Food Intake in Humans"; Am. J. Physiol. Regul. Integr. Comp. Physiol.; V. 285; pp. 992-998; 2003.

Naslund et al.; "Prandial Subcutaneous Injection of Glucagon-Like Peptide"; Br. J. Nutr.; V. 91; pp. 439-446; 2004.

Renshaw et al. "Peptide YY: A Potential Therapy for Obesity"; Current Drug Targets; V. 6; pp. 171-179; 2005.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; 2001.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

\* cited by examiner

APPARATUS AND METHOD FOR REMOTE DEFLATION OF INTRAGASTRIC BALLOON

CROSS-REFERENCE

This application is a continuation-in-part of U.S. application Ser. No. 11/735,194, filed Apr. 13, 2007, and claims the benefit of PCT application Ser. No. PCT/US08/059766, filed Apr. 8, 2008, the entirety of each of which is incorporated herein by this specific reference.

BACKGROUND OF INVENTION

1. Field of the Invention

The present invention is directed to devices and methods that enable remote deflation of intragastric balloons used for the treatment of obesity, and in particular devices and methods that enable an implanted intragastric balloon to be remotely deflated while the device itself is in the stomach.

2. Description of the Related Art

Intragastric balloons are well known in the art as a means for treating obesity. One such inflatable intragastric balloon is described in U.S. Pat. No. 5,084,061 and is commercially available as the BioEnterics Intragastric Balloon System (sold under the trademark BIB®). These devices are designed to provide therapy for moderately obese individuals who need to shed pounds in preparation for surgery, or as part of a dietary or behavioral modification program.

The BIB System, for example, comprises a silicone elastomer intragastric balloon that is inserted into the stomach and filled with a fluid, for example, a saline solution or air. The intragastric balloon functions by filling the stomach and enhancing appetite control. Placement of the intragastric balloon is non-surgical, usually requiring no more than 20-30 minutes. The procedure is performed gastroscopically in an outpatient setting, typically using local anesthesia and sedation. Placement is temporary, and intragastric balloons are typically removed after six months.

Most intragastric balloons utilized for this purpose are placed in the stomach in an empty or deflated state and thereafter filled (fully or partially) with a suitable fluid. The balloon occupies space in the stomach, thereby leaving less room available for food and creating a feeling of satiety for the patient. Clinical results with these devices show that for many obese patients, the intragastric balloons significantly help to control appetite and accomplish weight loss.

Intragastric balloons typically are implanted for a finite period of time, usually lasting approximately six months. This time period may be shortened by a treating physician who wishes to alter the patient's treatment and remove the balloon prior to the six month period. In any event, at some point after the balloon has been surgically placed in the stomach, it will become desirable to remove the balloon from the stomach. One of the means of removing the balloon is to deflate it by puncturing the balloon, and either aspirating the contents of the balloon or allowing the fluid to pass into the patient's stomach. This means of removing saline from the balloon requires surgical intervention, through the use of a gastroscopic instrument. When the balloon is deflated in this manner, the balloon itself may be surgically removed using the gastroscopic instrument.

Alternatively, if the balloon is left in place beyond its designed lifetime, the acids present in a patient's stomach may erode the balloon to the point where it self-deflates. When this occurs, the deflated balloon may pass naturally through the patient's digestive system and be expelled through the bowel.

Those experienced in the art will readily appreciate that manipulating the balloon in situ in order to deflate the balloon can be difficult. This is because the balloon is slippery and positionally unstable. The usually spherical or ellipsoidal intragastric balloons may readily rotate in the stomach, making it difficult for a surgeon to manipulate the balloon in order to find a deflation valve, or to safely puncture the balloon using a surgical instrument.

It may become desirable, then, particularly when the balloon is to be removed from the body, to cause the deflation of the balloon remotely without surgical intervention.

Therefore, the present invention is directed at overcoming the problems associated with the prior art systems. These and other objects of the present invention will become apparent from the further disclosure to be made in the detailed descriptions given below.

SUMMARY OF THE INVENTION

The present invention addresses the above-described problems by providing systems and methods for facilitating weight loss in a human or animal patient which are minimally invasive or non-invasive. Advantageously, the invention provides remotely deflatable intragastric balloon systems that allow a physician to remotely deflate an intragastric balloon implanted or positioned in a digestive tract, for example, a stomach of a patient, using a simple activation signal provided by a remote control.

In a broad aspect of the invention, systems are provided for facilitating weight loss which include an inflatable intragastric balloon for placement in a stomach of a patient, and a remotely activatable valve mechanism for deflating the balloon when it is desirable to remove the balloon from the patient.

The valve mechanism may comprise a heat deformable element, for example, a meltable wax plug, that when heated is caused to deform or melt, effectively opening the valve. Upon receipt of an activation signal sent by the physician from a remote control outside the body, microelectronics contained in the valve assembly cause the temperature of heating element(s) contained within the valve mechanism to melt the wax plug. Once the wax plug has melted, thus causing the balloon valve to open, the normal movements of the stomach cause the fluid contained within the balloon to empty from the balloon, causing deflation. The patient is able to then pass the balloon.

In another embodiment, the apparatus of the present invention includes a remote deflation valve having a shape memory element spring that holds a plug in place, thus sealing the valve of the intragastric balloon. The shape memory element spring may be heated remotely by induction, or the deflation mechanism may include microelectronics to cause heating of the spring. As the spring changes shape as a result of the application of heat, it removes the plug, thus causing the balloon to unseal. The fluid contained in the balloon may then flow freely out of the balloon, thus causing the balloon to deflate. The patient is then able to safely pass the deflated balloon.

According to yet another embodiment of the present invention, the intragastric balloon includes a remote deflation mechanism with a shape memory element actuator, a spring collar, an obstruction that holds the spring collar in place and a slit valve. As with the other embodiments disclosed, the shape memory element actuator may be heated remotely by induction or may alternatively include microelectronics and heating elements contained within the deflation mechanism. When the deflation mechanism is activated, the actuator pushes the obstruction out of the valve, thus allowing the spring collar to contract. The contraction of the spring collar causes the slit valve to open, which allows fluid contained in the balloon to flow out of the balloon and drain accordingly. The patient is then able to pass the deflated balloon.

In another preferred embodiment of the present invention, a shape memory element "cutting wire" is employed in the remote deflation mechanism. In this embodiment, when heat is applied to the shape memory alloy wire contained within a remote deflation valve, the wire changes shape, causing the wire to cut through a wax (or other suitable material, e.g. plastic or polymer) plug that seals the valve. Once the wax plug has been cut from the valve, fluid is able to freely flow through the valve, thus allowing the balloon to drain and pass from the body.

In still yet another preferred embodiment of the present invention, the remote deflation mechanism of the intragastric balloon includes a wire that surrounds the valve. The wire is used to break the bond between the valve and the balloon. When the bond between balloon and the valve is broken, the valve separates from the balloon, and fluid flows freely from the balloon. This preferred embodiment has the added benefit that the balloon and valve assembly may pass through the body separately, thus allowing passage to occur more easily, as the device is in two separate pieces. These and various other aspects of the invention, and its advantages, will be discussed in more detail below.

In another embodiment, the valve could be contained in a capsule, for example a substantially cylindrical or other shaped capsule (taking the shape of a large pill, for example) that fits within an opening in the shell, for example, a collared opening of the shell to create a seal. The collared opening could include a resilient element, for example a spring or other such mechanism that would substantially retain the size and/or shape of the collar. When the valve mechanism is activated, the resilient element is released, thereby opening the collar and ejecting the capsule from the balloon, rendering two separate components that could then easily pass through the gastrointestinal track of the patient. Alternatively, the collared opening could include a heating element, which when the remote deflation mechanism is activated, would cause the bond between the capsule and the collar to break, thereby ejecting the capsule from the shell. As yet a further alternative, the capsule could contain a resilient element such as a spring, for example, a torsional spring, that retains the shape and/or size of the capsule, holding the capsule in place within the opening of the shell. When the remote deflation mechanism is activated, the torsional spring is causes to collapse or otherwise deform, breaking the bond and causing the capsule to be ejected from the shell.

Each and every feature described herein, and each and every combination of two or more of such features, is included within the scope of the present invention provided that the features included in such a combination are not mutually inconsistent.

These and other features, aspects and advantages of the present invention will become apparent hereinafter, particularly when considered in conjunction with the following claims, detailed description and drawings in which like parts bear like reference numerals.

DETAILED DESCRIPTION

The present invention is directed to remotely deflatable intragastric balloons and methods for deflating intragastric balloons, for example, remotely and without surgical intervention.

Figure 1:
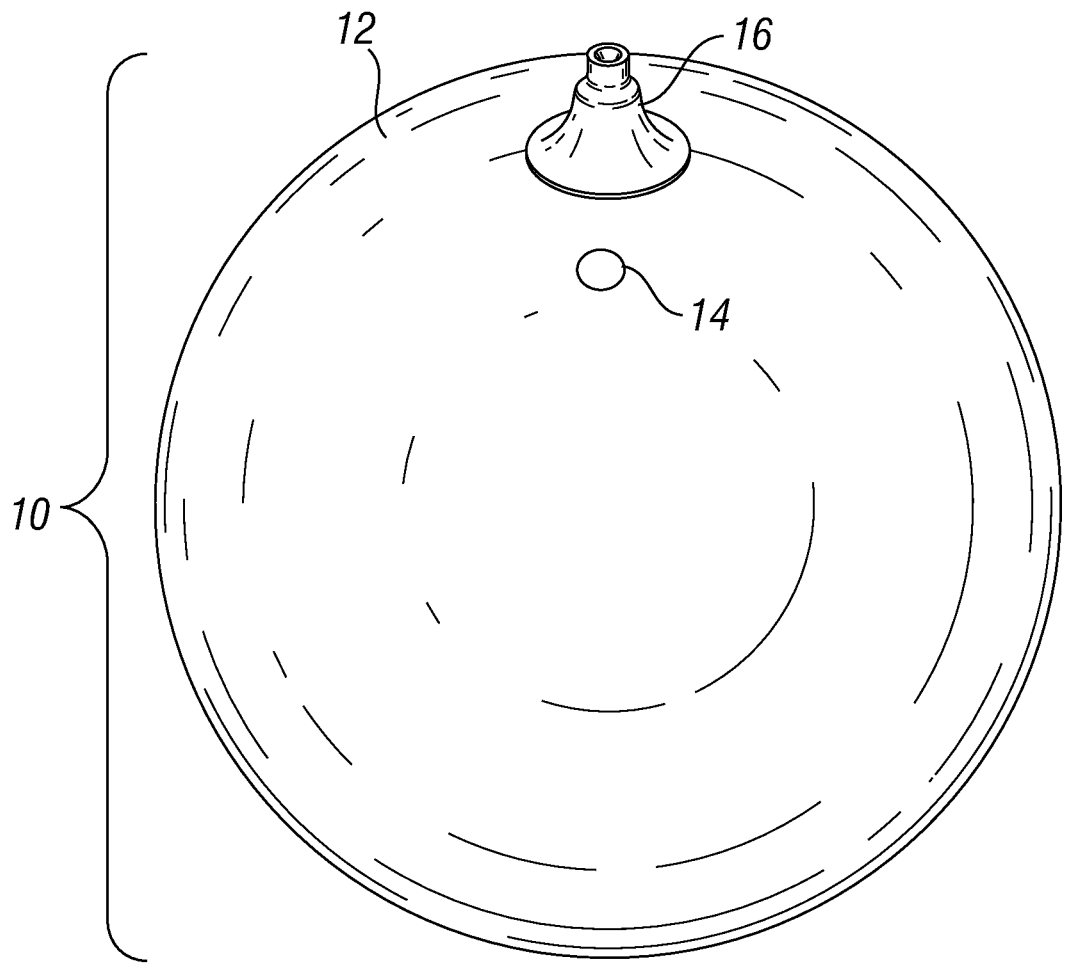
FIG. 1 is an elevated side view of an intragastric balloon of the present invention.
Figure 9:
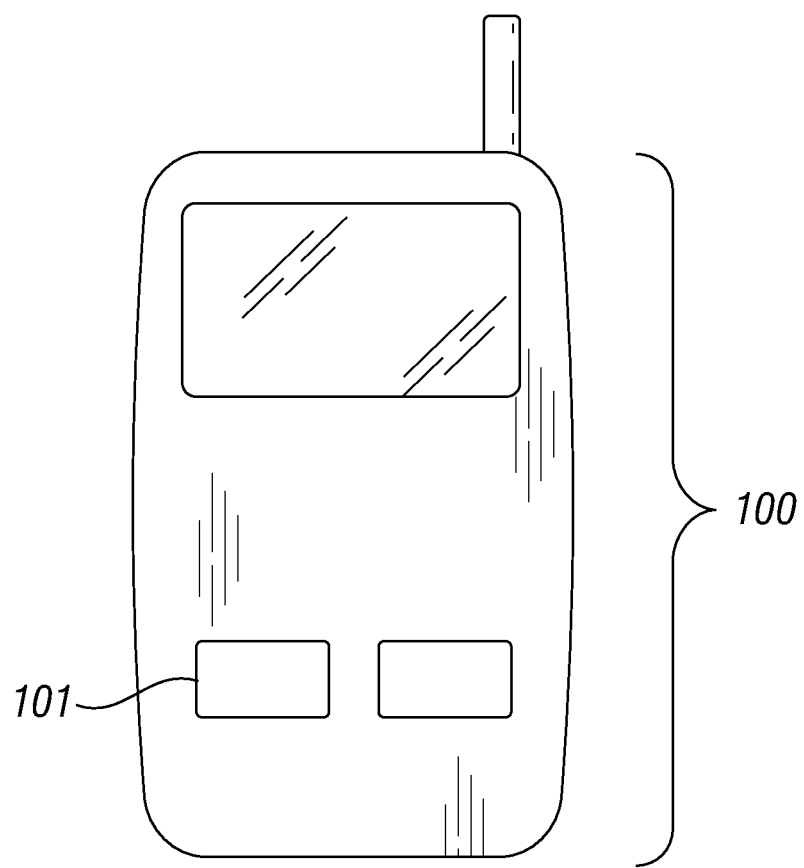
FIG. 9 is a front view of a remote control for activating a remote deflation valve according to the present invention.

Referring to FIG. 1, an intragastric balloon in accordance with the invention is shown generally at 10. The intragastric balloon 10 generally comprises a shell 12 and a remotely activatable valve mechanism 16 coupled to the shell 12. Turning now briefly as well to FIG. 9, in a typical embodiment, the intragastric balloon 10 is a component of a remotely deflatable intragastric balloon system in accordance with the present invention, the system generally comprising intragastric balloon 10 and a remote control 100. As will be explained further hereinafter, the remote control 100 and valve mechanism 16 are effective to cause or at least initiate or facilitate remote deflation of the shell 12 while the balloon 10 is located in a stomach or other part of the gastrointestinal tract of a patient.

The balloon 10 is sized, shaped and otherwise structured to be suitable for placement in a digestive track of a patient, for example, in a stomach of human or animal patient. The shell 12 is capable of being inflated with a fluid, for example, a liquid or gas, so that the balloon 10 will safely occupy space in the stomach. The shell 12 may comprise any suitable material, for example, a flexible or expandable biocompatible material suitable for placement in a gastrointestinal tract of a human being or animal.

During implantation, the balloon 10 in an un-inflated state is placed in the stomach in a desired location. Once the balloon 10 is positioned, it is then inflated, for example, using valve 16, or an alternate fill valve 14. Those experienced in the art will appreciate that there are several different methods for inflating the balloon 10, such as disclosed in commonly assigned International Application Number PCT US03/19414, entitled "Two Way Slit Valve", the disclosure of which is incorporated in its entirety herein by reference.

When it becomes desirable to remove the balloon 10 from the patient, the balloon 10 must typically be deflated, for example, emptied, or at least partially emptied, of the fluid in the shell 12. Preferably, the present invention is designed such that the deflated intragastric balloon 10 does not require physician intervention for removal, in that it will be able to safely and naturally pass through the digestive system and from the patient's body. Alternatively, the deflated balloon 10 may be removed using a minimally invasive gastroscopic procedure.

Figure 2A:
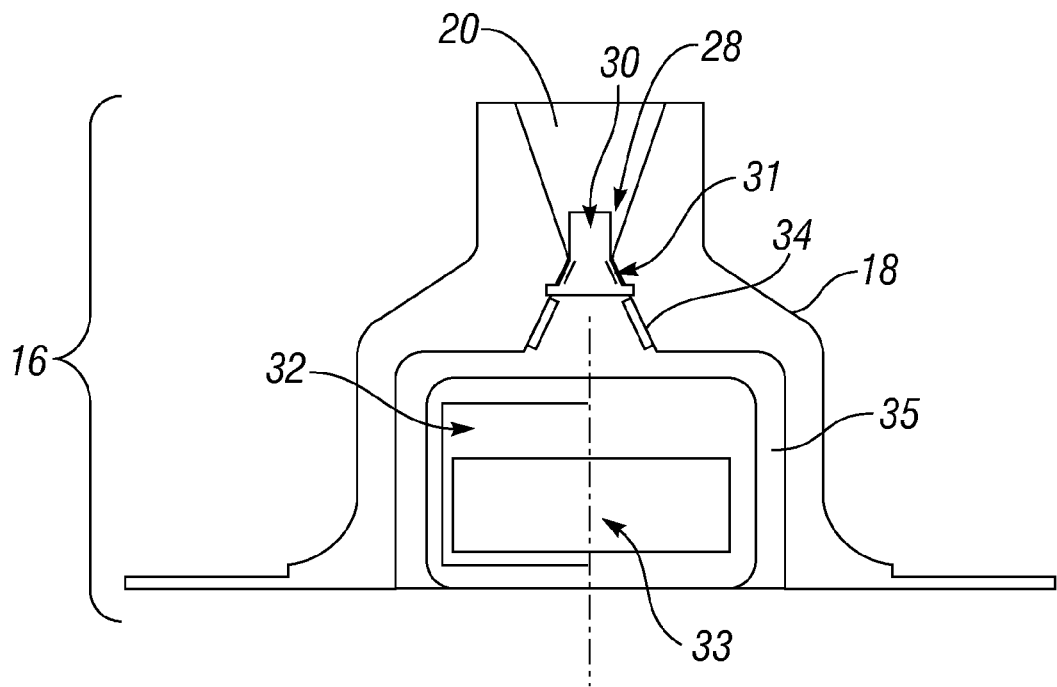
FIG. 2a is a side cut-away view of a remote deflation valve according to one embodiment of the present invention, which shows the valve in the "closed" position.
Figure 2B:
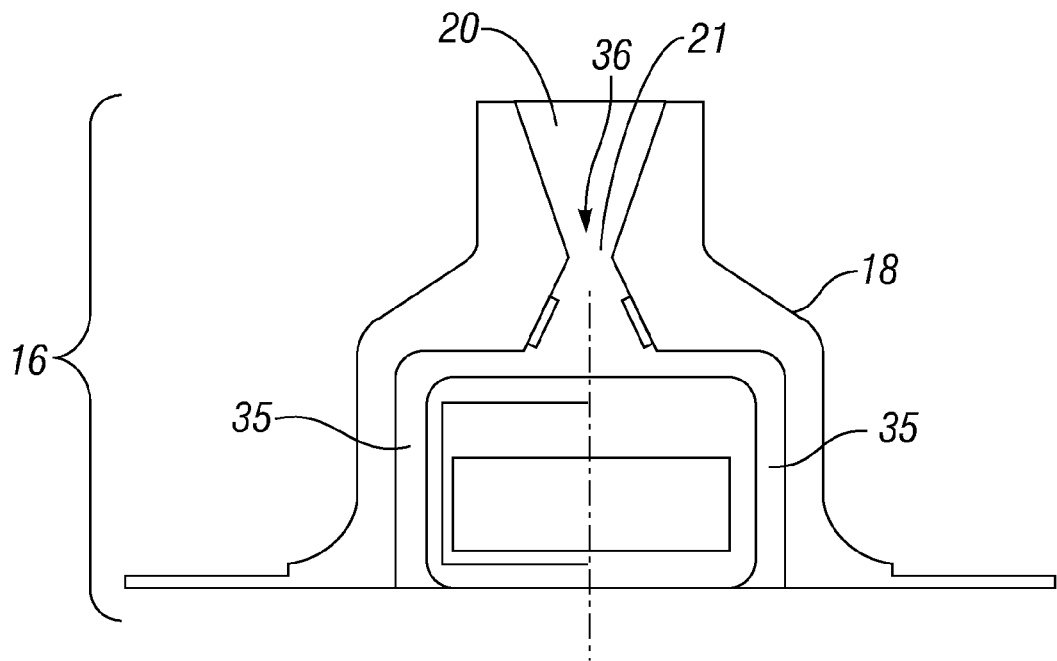
FIG. 2b is a side cut-away view of the remote deflation valve of FIG. 2a shown in the "open" position.

Referring to FIGS. 2a and 2b, one embodiment of the remotely activatable valve mechanism 16 in accordance with present invention is shown. Valve mechanism 16 may comprise a housing 18 defining a channel 20, and a deformable element, for example a heat deformable plug 30 made of wax or other suitable material, sealed within the channel 20. In the shown embodiment, the channel 20 includes a neck portion 21 in which plug 30 is disposed, and capillaries 35 in fluid communication with an interior of the shell (not shown in FIGS. 2a and 2b). Plug 30 is preferably formed of suitable medical-grade wax, such as paraffin, or may be alternatively formed of a low temperature melt polymer.

The valve 16 includes an actuator 28 comprising one or more heating element(s) 31 in contact with, or at least in thermal communication with, plug 30.

In this exemplary embodiment, the actuator 28 further comprises a controller/receiver example, a microelectronic signal receiver 32 and a power source 33. The receiver 32 includes an antenna and/or other suitable microelectronics capable of receiving a signal transmitted from the remote control (FIG. 9) and energizing the heat elements 31. The remote control 100 and actuator 28 may be structured to operate via radio waves, sonic waves, or other electromagnetic signal transmission/receiving means that can be safely transmitted from the remote control through the tissue of the patient to the implanted balloon 10. The power source 33 may comprise a battery, capacitor, induction coil, kinetic energy creation by body motion stored onto a capacitor, fuel cell, power source powered by chemistry of the body, or a power source powered by temperature change. In some embodiments, the actuator 28 is structured to be powered by a remote power source, such as by magnetic coupling from an external source to an internal, or implanted, inductor coil.

When in use, at the time the physician desires to deflate the implanted balloon 10, the patient may be brought into the physician's office in an outpatient setting. In order to activate valve 16 and initiate emptying of the fluid from the shell 12, the physician uses the remote control 100 (FIG. 9) to send an activation signal to the receiver 32. For example, the physician holds remote control 100 near the stomach or abdomen of the patient. Upon depression of button 101, remote control 100 effectuates deflation of the shell 12 by causing actuator 28 to energize heating elements 31 which melt or otherwise deform the plug 30 thereby releasing or breaking the seal between the plug 30 and the channel 20. Once the seal has been broken, fluid within the shell 12 begins to evacuate the balloon 10 through the channel 20 of the valve mechanism 16. Release of the fluid from the shell 12 causes quenching or cooling of the heating elements 31. Through normal body movements, for example, contractions of the stomach walls, the unsealed balloon 10 will drain of a majority or all of the fluid, and the shell 12 will reduce to a size that is passable through the patient's digestive tract. The microelectronics, heating element, and power source (if provided) are safely contained by the structure of the valve mechanism such that these components too will easily pass without presenting a danger to the patient.

In this embodiment, deformation or melting of the plug 30 is caused by the rise in temperature at sealing surface of the plug 30. The plug 30 comprises a material that will begin to melt or deform when subjected to heat at a temperature slightly above the normal temperature within the stomach. For example, the plug 30 may comprise a paraffin wax having a melting point of one or more degrees above, the normal body temperature of the stomach in order that the valve will remain sealed or closed until purposefully activated.

Once the seal between the plug 30 and the channel 20 has been broken, the plug 30 is expelled into the stomach. In some embodiments, the valve mechanism 30 further includes a mechanism or structure effective to collect melted plug material. For example, the valve mechanism 16 may comprise one or more wicking surfaces 34, for example, located within the channel 20. Wicking surfaces 34 may comprise a suitable material for collecting the plug material and/or may simply be in the form of a contoured collection reservoir. The collection of the plug material on wicking surfaces 34 may facilitate prevention of melted material from clogging the channel 20.

In one optional aspect of the invention, in addition to performing the function of activating the heating elements 31, the valve mechanism 16 may include electronics capable of transmitting a signal, for example a confirmation signal, to the remote control 100, to confirm that the valve mechanism 16 has been activated or deflation of the balloon 10 has been initiated. Following receipt of a confirmation signal, the physician and/or patient may then track the position or progress of the passing of the balloon 10.

Figure 3A:
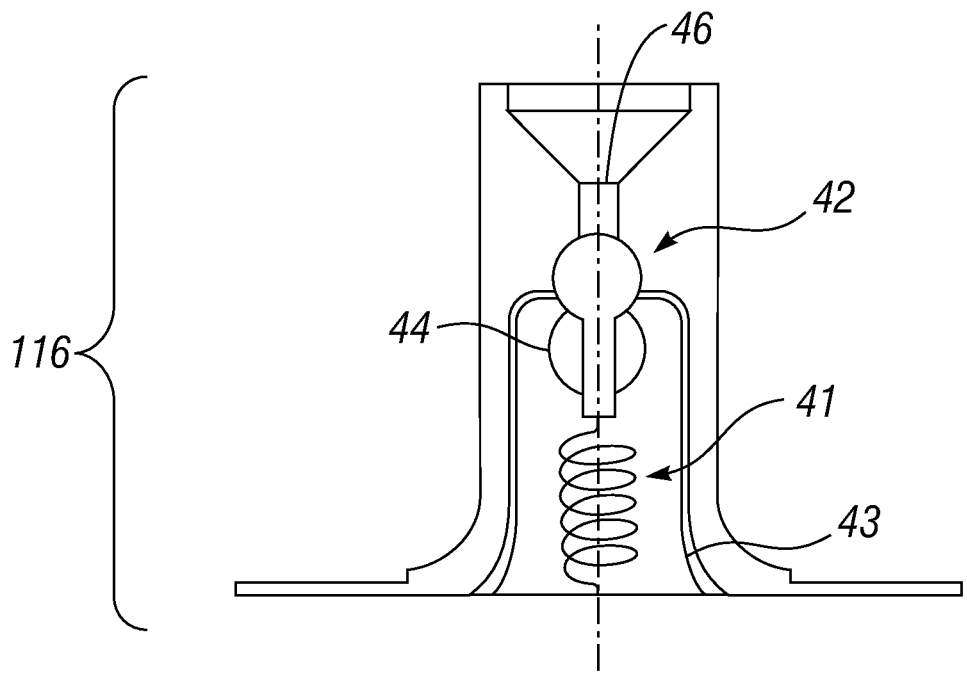
FIG. 3a is a side cut-away view of a remote deflation valve according to a further embodiment of the present invention, which shows the valve in the "closed" position.
Figure 3B:
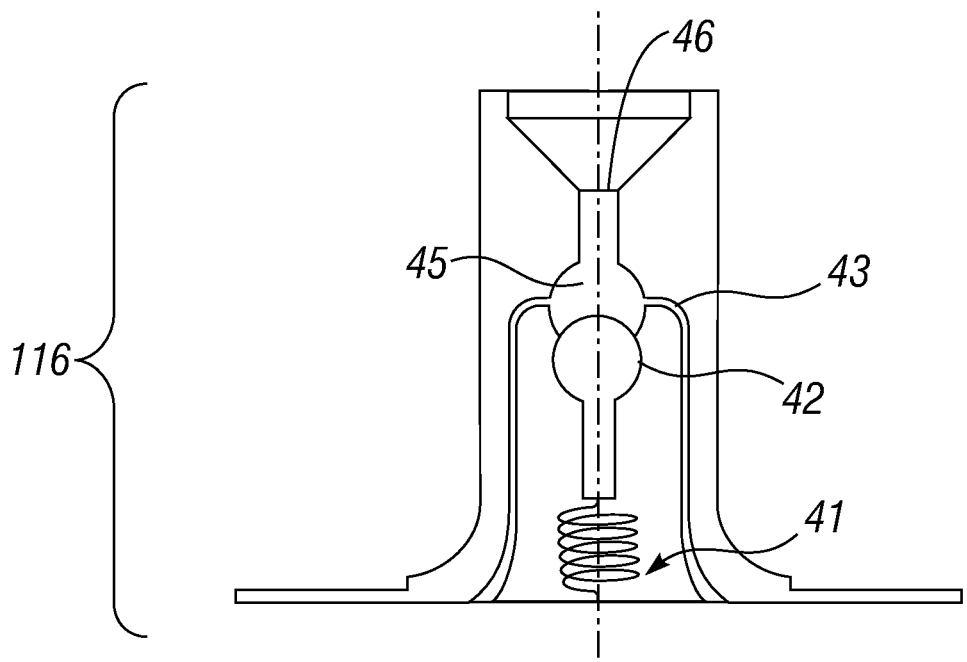
FIG. 3b is a side cut-away view of the remote deflation valve of FIG. 3a shown in the "open" position.

Referring to FIGS. 3a and 3b, an alternative remotely activated valve mechanism 116 in accordance with the present invention is shown. More specifically, FIG. 3a shows the valve in a closed or sealed position, and FIG. 3b shows the valve in an open or unsealed position. Remotely activated valve mechanism 116 has substantially the same purpose as remotely activated valve mechanism 16 described elsewhere herein but operates somewhat differently therefrom.

Valve mechanism 116 generally comprises a heat deformable element, for example, spring 41, and a plug 42 coupled to the spring 41. In the closed state of valve mechanism 116, spring 41 maintains plug 42 in the closed position shown in FIG. 3a, such that an enlarged portion of the plug 42 is seated in region 45 (region 45 shown more clearly in FIG. 3b) of channel 46, and seals or blocks capillaries 43 from fluid flow.

Spring 41 may comprise a shape memory material, for example, a shape memory alloy, for example, Nitinol, or other suitable material. Upon application of heat to spring 41, for example, such as described elsewhere herein using remote control 100 (FIG. 9) and heating elements (not shown in FIGS. 3a and 3b), spring 41 is caused to deform, for example contract, and moves or releases plug 42 from the sealed position (FIG. 3a) to an open, unsealed position, such as shown in FIG. 3b. When plug 42 is in the unsealed position, the enlarged portion of the plug 42 is held in holding region 44 of the channel 46 and region 45 of channel 46 is open, allowing the fluid contained in the balloon 10 to flow through the capillaries 43 and out of the valve mechanism 116.

As an alternative to having a shape memory spring permanently fixed to a plug, the spring may be detachably fixed to a plug comprised of wax or some other similar biodegradable material. In this way, when the spring is heated and changes shape, it may be used to eject the biodegradable plug into the stomach, thus allowing the balloon to drain. The deflated intragastric balloon would then be allowed to pass out of the body.

Referring to FIGS. 4a, 4b, 5a, and 5b, another embodiment of a remotely activated valve mechanism 216 of the present invention is shown. Remotely activated valve mechanism 216 has substantially the same purpose as remotely activated valve mechanism 16 described elsewhere herein but operates somewhat differently therefrom. More specifically, valve mechanism comprises a slit valve. For example, valve mechanism 216 may include many of the features of the device described in WO 2005/007231 having international publication date of Jan. 27, 2005, which is incorporated herein in its entirety by this specific reference.

Figure 5A:
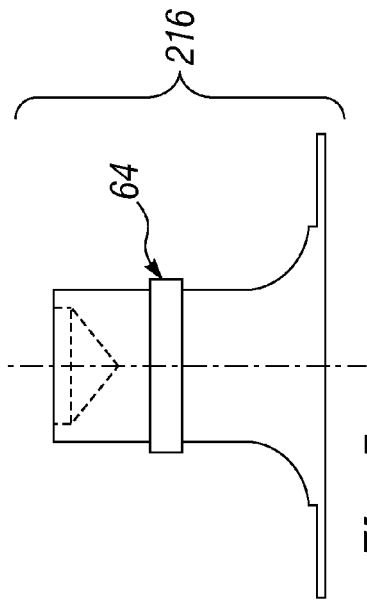
FIG. 5a is a side view of the remote deflation valve of FIG. 4a which shows the valve in the "closed" position.
Figure 5B:
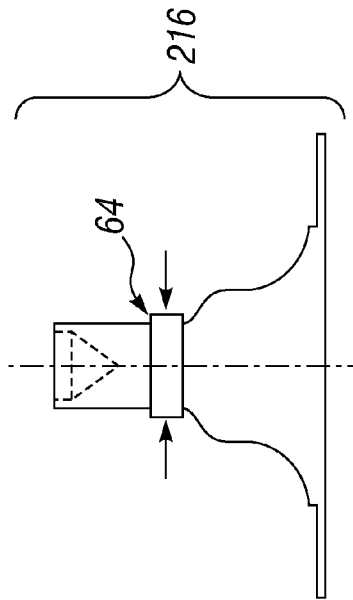
FIG. 5b is a side view of the remote deflation valve of FIG. 4b shown in the "open" position.
Figure 4A:
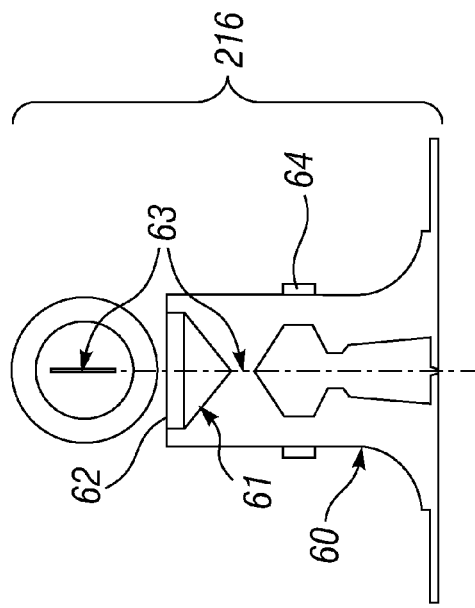
FIG. 4a is a side view of a remote deflation valve according to yet a further embodiment of the present invention, which shows the valve in the "closed" position.
Figure 4B:
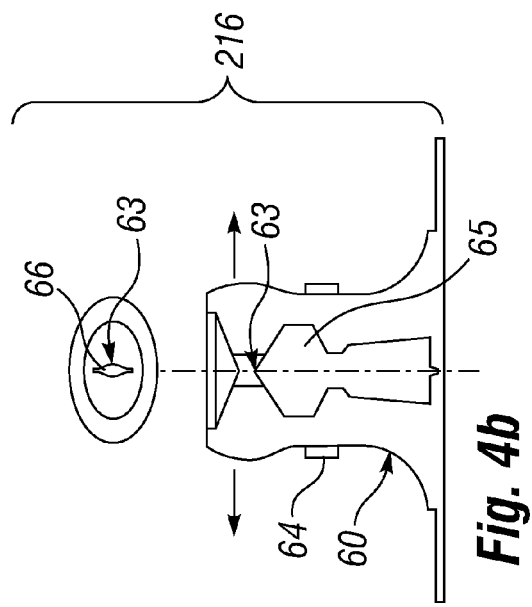
FIG. 4b is a side cut-away view of the remote deflation valve of FIG. 4a shown in the "open" position.

FIGS. 4a and 4b show a cutaway side view of valve mechanism 216 in closed and open positions respectively, while FIGS. 5a and 5b show the same valve mechanism in closed and open positions respectively, in a different side view. Valve mechanism 216 generally comprises an elastomeric valve body 60 having a division or slit 63, and an actuator, for example, a shape memory element which is structured or positioned to open or enlarge the slit when the shape memory element deforms or contracts. More specifically, the shape memory element may be in the form of a collar, for example, a spring collar 64 disposed at least partially around the valve body 60. In some embodiments, the valve mechanism 216 optionally includes an obstruction 62 seated in a distal opening 61 and providing, for example, enhanced sealing of the valve mechanism 216 when in the closed position.

When heated, such as described elsewhere herein, the collar 64 contracts, compressing the elastomeric valve body 60, and causing the slit to enlarge or open, to establish fluid communication between channel 65 and distal opening 61. In embodiments having obstruction 62 sealing the distal opening, the contraction of the collar 64 causes obstruction 62 to be ejected or otherwise unseated from the opening 61.

An alternative construction in this embodiment includes a collar or other constricting element positioned and shaped to contract the slit valve on two points along the housing along or on the axis of the slit. This would allow the constricting element to pinch the slit open and create an open fluid path to allow fluid to drain from the balloon. The constricting element may be an oval or elliptical shaped collar or other construction which, when contracted, operates to constrict and pinch the valve open, for example, along a short axis of the oval or ellipse.

With valve mechanism 216 in the open position (FIG. 4b), the fluid contained in the balloon (not shown) will flow through channel 65 and out through the opening 66 (FIG. 4b) of valve mechanism 216, thus causing the balloon to deflate. The deflated intragastric balloon is then allowed to pass out of the body.

Figure 6A:
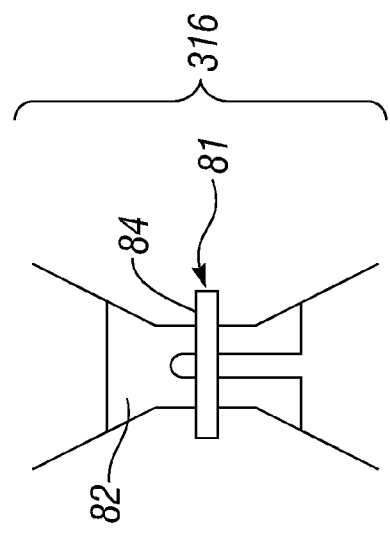
FIG. 6a is a side cut-away view of a remote deflation valve according to still a further embodiment of the present invention, which shows the valve in the "closed" position.
Figure 6B:
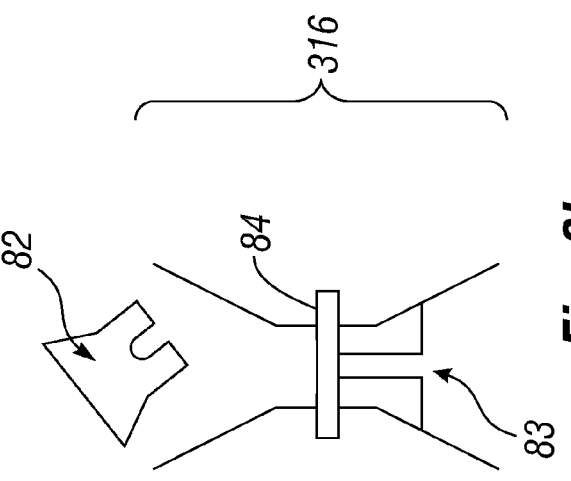
FIG. 6b is a side cut-away view of the remote deflation valve of FIG. 6a shown in the "open" position.

Referring to FIGS. 6a and 6b, an interior cutaway view of another remotely activatable valve 316 of the present invention is shown. Remotely activated valve mechanism 316 has substantially the same purpose as remotely activated valve mechanism 16 described elsewhere herein but operates somewhat differently therefrom.

Valve mechanism 316 generally comprises a cutting mechanism 81, severable sealing plug 82, and capillary 83 extending partially through sealing plug 82. Cutting mechanism 81 includes a wire 84 capable of severing the sealing plug 82. Wire 84 may comprise a shape memory alloy such as described elsewhere herein.

As heat is applied to the wire 84, for example, by heating elements 85 such as described elsewhere herein, the wire 84 changes shape, which in turn causes the wire 84 to cut through the sealing plug 82 and open capillary 83 to fluid flow.

Figure 7B:
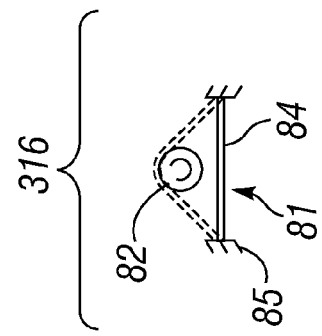
FIGS. 7a and 7b show a top view of an embodiment of the wire cutting mechanism of the remote deflation valve of FIGS. 6a and 6b.
Figure 7D:
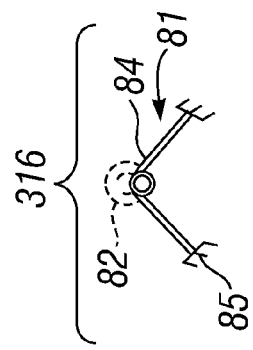
FIGS. 7c and 7d show a further embodiment of the wire cutting mechanism of the remote deflation valve of FIGS. 6a and 6b.
Figure 7A:
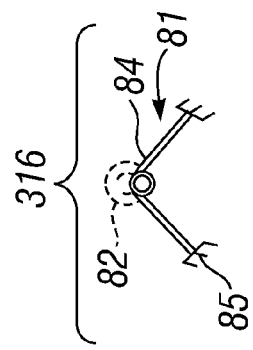

For example, FIG. 7a shows the cutting mechanism 84 prior to the application of heat, such that wire 81 is in a curved L-shape, with a curved portion resting adjacent the severable sealing plug 82.

In this embodiment, cutting mechanism 81 is activated by a signal received from remote control 100 (FIG. 9) to cause an increase in temperature of the wire 84. The increase in temperature causes wire 84 to change shape such that it slices through the sealing plug 82, such as shown in FIG. 7b.

Figure 7C:
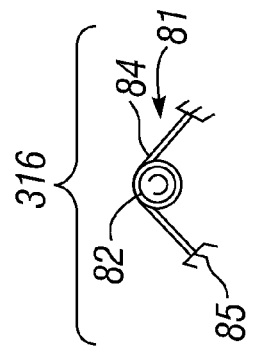

Alternatively, the shape memory wire 84 may be disposed in loop shape that encircles the severable sealing plug 82, such as shown in FIG. 7c. Upon heating of wire 84, the wire is caused to change shape such that it takes the shape shown in FIG. 7d, having a smaller looped portion, thereby slicing through the severable sealing plug 82.

Figures 8A, 8B:
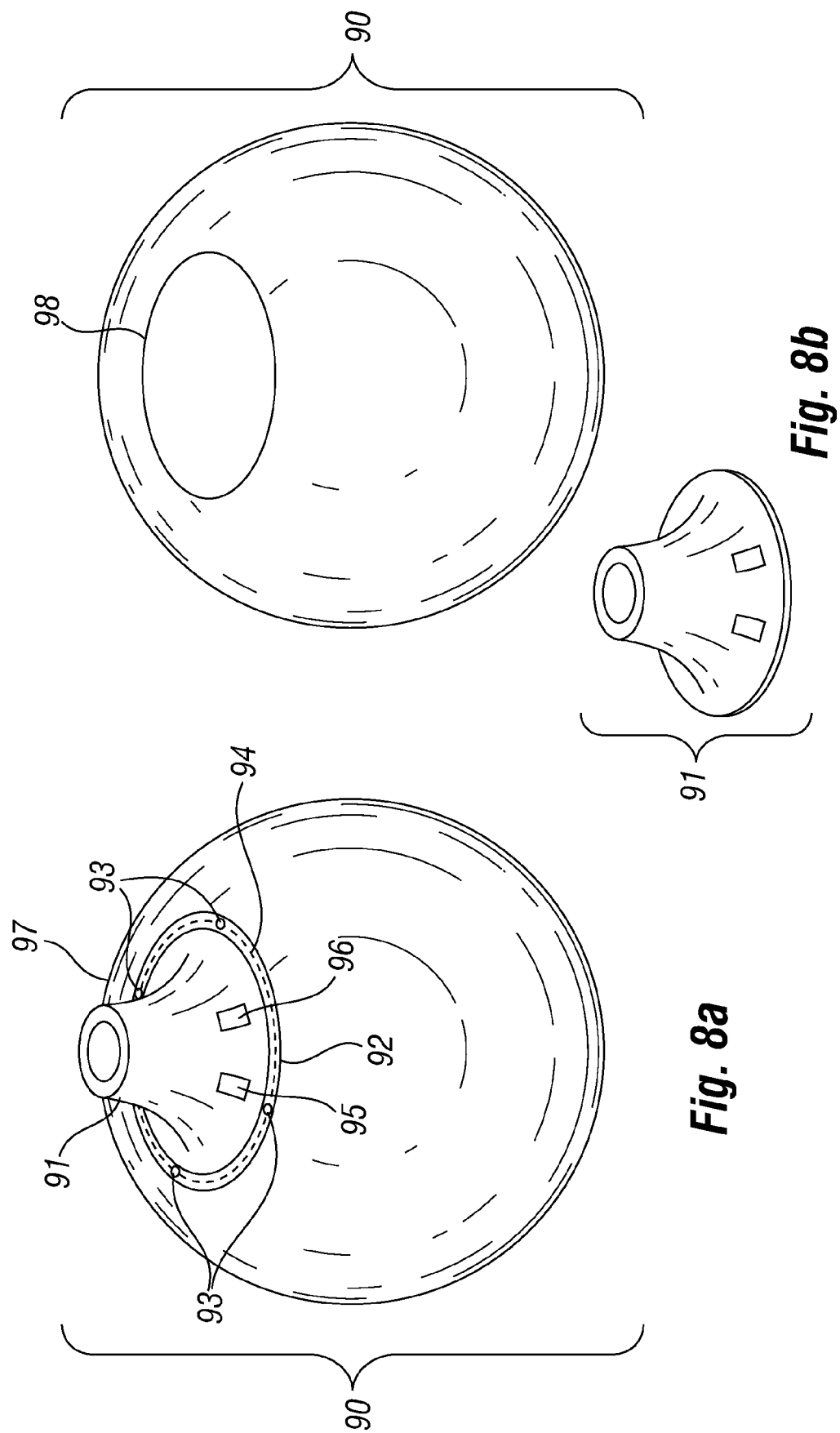
FIG. 8a shows an elevated side view of an intragastric balloon of the present invention with a deflation mechanism surrounding the valve prior to the deflation mechanism being activated.
FIG. 8b shows an elevated side view of FIG. 8a after the deflation mechanism has been activated.

Referring to FIGS. 8a and 8b, another preferred embodiment of an intragastric balloon of the present invention incorporating a remotely activated valve mechanism is shown. Intragastric balloon 90 generally comprises shell 97, valve 91, valve/balloon bond 92, heating elements 93, wire 94, microelectronic control 95, and power source 96.

The embodiment of the present invention shown in FIGS. 8a and 8b utilizes a remote activation to separate the valve 91 from the remaining portion of the balloon 90.

More specifically, in order to cause the balloon 90 to deflate, the physician using for example, remote control 100 (FIG. 9) sends an activation signal to the microelectronic control 95.

Microelectronic control 95 includes a receiver or antenna (not shown) for receiving the activation signal from remote control 100. Upon receiving the activation signal, microelectronic control uses power from power source 96 to begin increasing the temperature of heating element(s) 93. Similar to the embodiments discussed above that incorporate heating elements, metal film heating elements utilizing materials such as nichrome, stainless steel, copper, gold, or other such materials, can be used for heating element(s) 93. As heating element(s) 93 begin to increase in temperature, the temperature of wire 94 also increases. The increased temperature of the wire causes valve/balloon bond 92 to deteriorate, resulting in separation of the valve 91 from shell 97.

Once the valve/balloon bond 92 is broken and the valve is separated from the shell, fluid contained inside the balloon flows through the opening 98 (see FIG. 8b) that is created by the separation of the two portions. Through the normal movements and contraction of the stomach walls, the balloon will drain of the fluid contained inside and shrink down to a size that is passable through the human body. The microelectronics, heating element(s) and power source are safely contained within the valve structure such that they do not present any danger to the patient. Because the entire intragastric balloon may now be in two separate pieces—an empty shell and a self-contained valve assembly—the passing of the balloon and valve is facilitated.

As with the previous embodiments described, in addition to performing the function of controlling the heating elements, the microelectronic control 95 may communicate with the remote control 100 to confirm that the deflation mechanism has been activated. Following receipt of a confirmation signal, the physician and patient may then track the progress of the passing of the device.

Figure 10A:
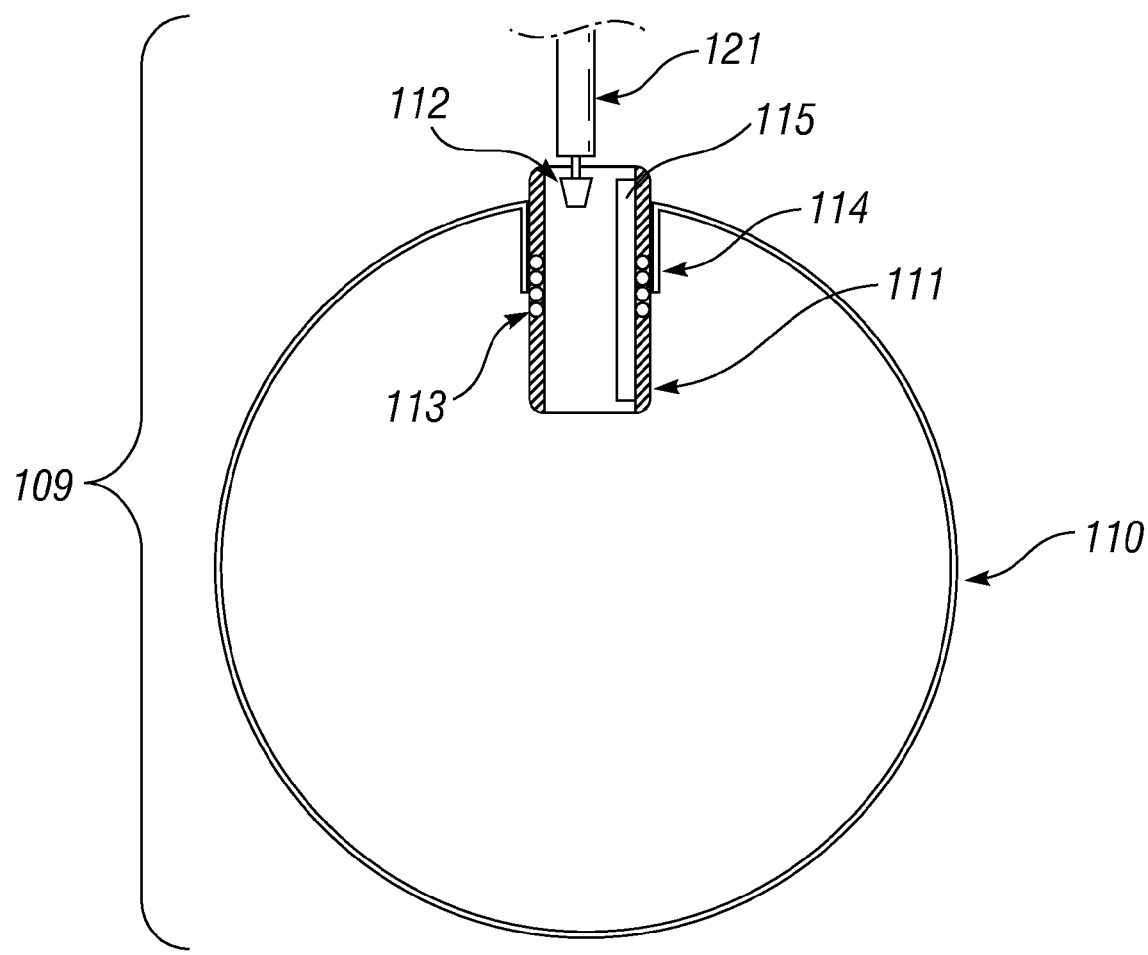
FIG. 10a is a side cut-away view of a remote-deflating intragastric balloon according to still a further embodiment of the present invention, which shows the balloon in the "closed" position.
Figure 10B:
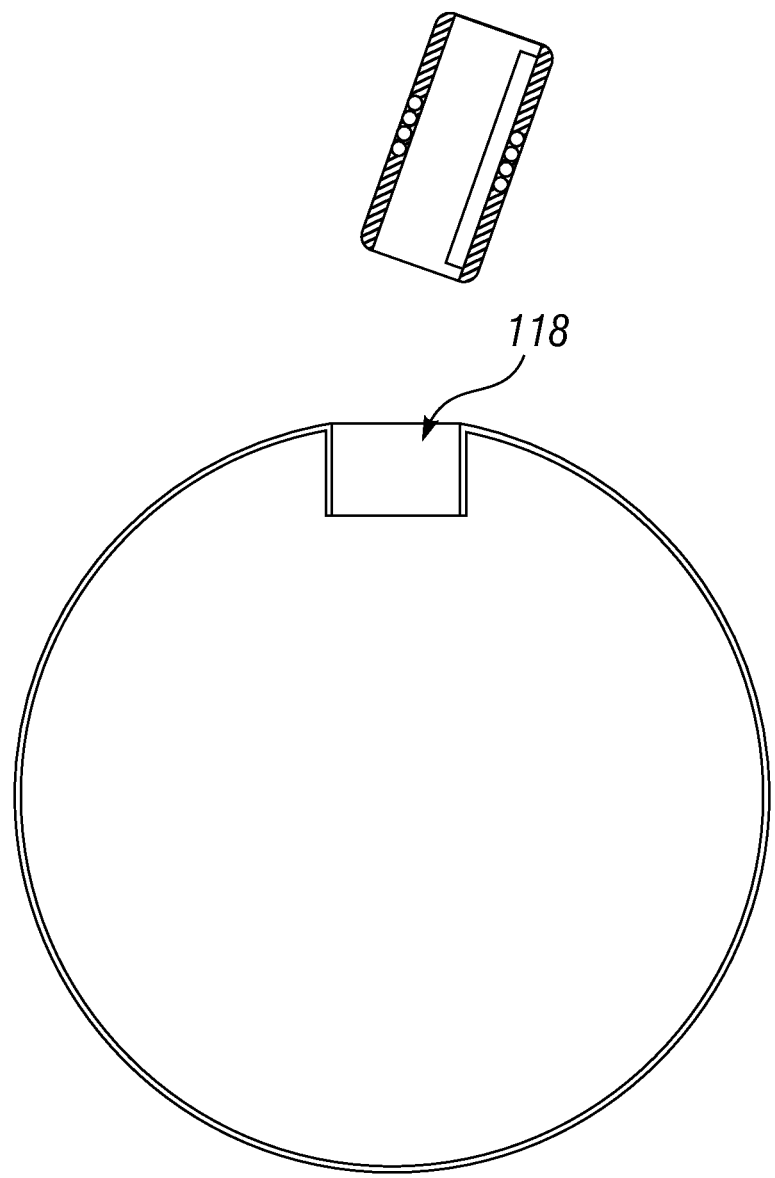
FIG. 10b is a side cut-away view of the remote-deflating intragastric balloon of FIG. 10a shown in the "open" position.

Referring to FIGS. 10*a* and 10*b*, another preferred embodiment of an intragastric balloon of the present invention incorporating a remote deflation mechanism is shown. Intragastric balloon 109 is comprised of shell 110 and valve capsule 111. Valve capsule 111 is comprised of valve 112, shape memory torsional spring 113, and combined microelectronic control and power source 115. FIG. 10*a* also shows adjustment tool 121 for adjusting the volume of the intragastric balloon 109.

Rather than using a remote deflation mechanism to open the valve of the intragastric balloon, the embodiment of the present invention shown in FIGS. 10*a* and 10*b* utilizes a deflation mechanism for separating the entire valve capsule from the remaining portion of the balloon. When inflated, the valve capsule 111 is held tightly in the balloon collar 114 by pressure exerted by shape memory torsional spring 113, creating a seal between the valve capsule and the balloon collar.

Similar to the various procedures described above, at the time the physician desires to deflate the balloon, the patient may be brought into the physician's office in an outpatient setting. In order cause the intragastric balloon 109 to deflate, the physician activates the valve opening mechanism remotely and from outside the body, using a remote control 100 (FIG. 9). The physician holds remote control 100 near the stomach of the patient, and upon depression of a button, remote control 100 sends an activation signal to the combined microelectronic control and power source 115.

Combined microelectronic control and power supply 115 has an antenna (not shown) for receiving the activation signal from remote control 100. Upon receiving the activation signal, combined microelectronic control and power source uses power to begin increasing the temperature of heating element(s) (not shown) that are connected to the torsional spring 113. Similar to the embodiments discussed above that incorporate heating elements, metal film heating elements utilizing materials such as nichrome, stainless steel, copper, gold, or other such materials, can be used for the heating element(s). As the temperature of the heating element(s) begin to increase, the temperature of shape memory torsional spring 113 also begins to increase, thereby causing the spring to deform and reduce in diameter. As the diameter decreases, the seal between valve capsule 111 and balloon collar 114 is broken.

Once the seal between the balloon collar 114 and valve capsule 111 is broken and the valve capsule is separated from the shell, fluid contained inside the balloon freely flows through the opening 116 (FIG. 10*b*) that is created by the separation of the two portions. Through the normal movements and contraction of the stomach walls, the balloon will drain of the fluid contained inside and shrink down to a size that is passable through the human body. The combined microelectronic control and power supply and heating element(s) are safely contained within the valve capsule such that they do not present a danger to the patient. Because the entire intragastric balloon may now be in two separate pieces—an empty shell and a self-contained valve capsule—the passing of the balloon and valve is facilitated.

As with the previous embodiments described, in addition to performing the function of controlling the heating elements, the combined microelectronic control and power supply 115 may communicate with the remote control 100 to confirm that the deflation mechanism has been activated. Following receipt of a confirmation signal, the physician and patient may then track the progress of the passing of the device.

Figure 11:
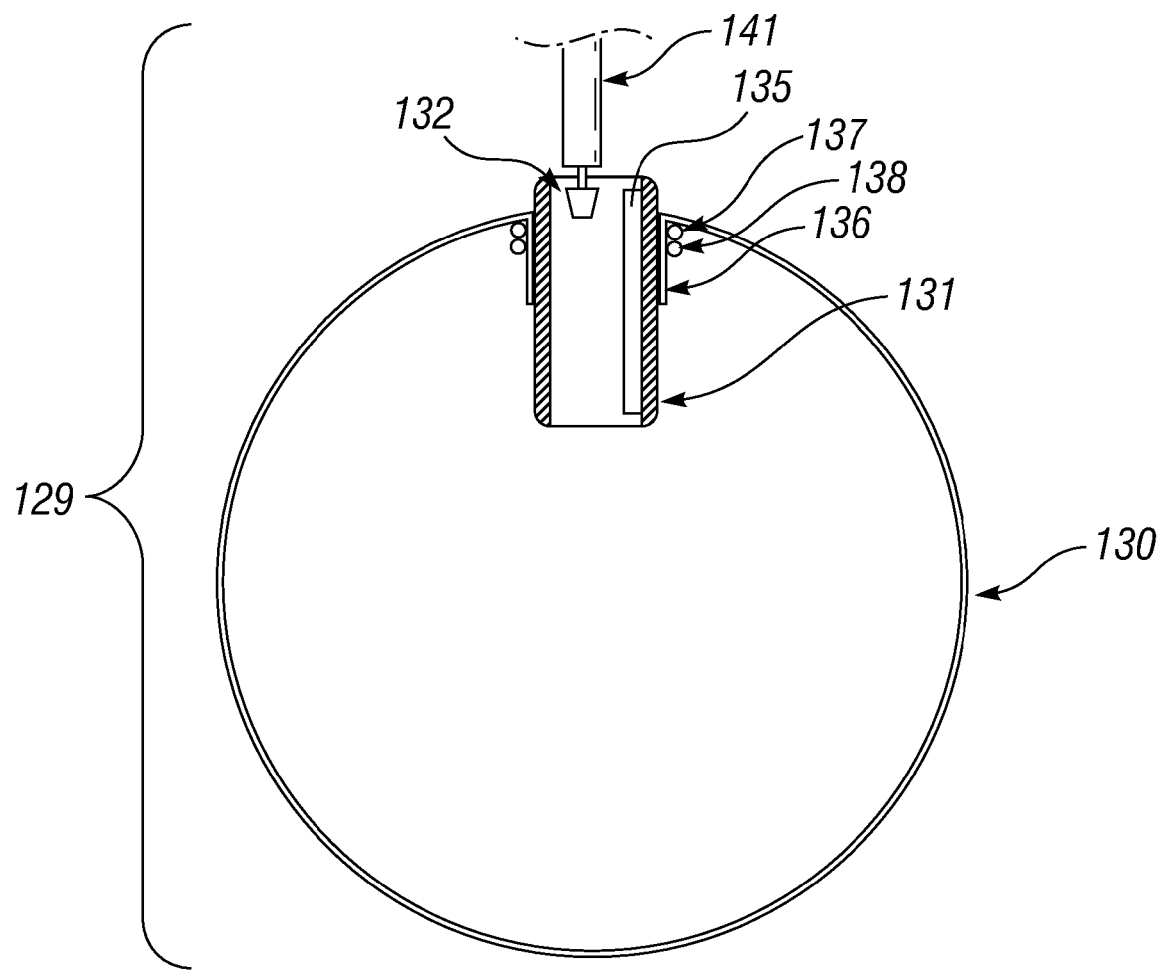
FIG. 11 is a side cut-away view of a remote-deflating intragastric balloon according to still a further embodiment of the present invention, which shows the balloon in the "closed" position.

Referring to FIG. 11, another preferred embodiment of an intragastric balloon of the present invention incorporating a remote deflation mechanism is shown. Intragastric balloon 129 is comprised of shell 130 and valve capsule 131. Valve capsule 131 is comprised of valve 132 and combined microelectronic control and power source 135. Shell 130 is comprised of a collar 136, heating element 137, and shape memory cutting element 138. FIG. 11 also shows adjustment tool 141 for adjusting the volume of the intragastric balloon 129.

As with several of the other embodiments previously discussed, rather than using a remote deflation mechanism to open the valve of the intragastric balloon, the embodiment of the present invention shown in FIG. 11 utilizes a deflation mechanism for separating the entire valve capsule from the remaining portion of the balloon. When inflated, the valve capsule 131 is held tightly in the balloon collar 114 by pressure exerted by shape memory element 138, creating a seal between the valve capsule and the balloon collar.

Similar to the various procedures described above, at the time the physician desires to deflate the balloon, the patient may be brought into the physician's office in an outpatient setting. In order cause the intragastric balloon 129 to deflate, the physician activates the valve opening mechanism remotely and from outside the body, using a remote control 100 (FIG. 9). The physician holds remote control 100 near the stomach of the patient, and upon depression of a button, remote control 100 sends an activation signal to the combined microelectronic control and power source 135.

Combined microelectronic control and power supply 135 has an antenna (not shown) for receiving the activation signal from remote control 100. Upon receiving the activation signal, combined microelectronic control and power source uses power to begin increasing the temperature of heating element(s) 137 that are connected to the shape memory cutting element 138. Similar to the embodiments discussed above that incorporate heating elements, metal film heating elements utilizing materials such as nichrome, stainless steel, copper, gold, or other such materials, can be used for the heating element(s). As the temperature of the heating element(s) begin to increase, the temperature of shape memory cutting element 138 also begins to increase, thereby causing the cutting element to cut through the balloon collar 136. With the balloon collar 136 completely cut, the seal between valve capsule 131 and balloon collar 136 is broken.

Once the seal between the balloon collar 136 and valve capsule 131 is broken and the valve capsule is separated from the shell, fluid contained inside the balloon freely flows through the opening that is created by the separation of the two portions. Through the normal movements and contraction of the stomach walls, the balloon will drain of the fluid contained inside and shrink down to a size that is passable through the human body. The combined microelectronic control and power supply and heating element(s) are safely contained within the valve capsule such that they do not present a danger to the patient. Because the entire intragastric balloon may now be in two separate pieces—an empty shell and a self-contained valve capsule—the passing of the balloon and valve is facilitated. As an alternative to the cutting mechanism described herein, the remote deflation mechanism may be comprised of a mechanical system (such as a torsional spring) contained within the collar which holds the valve capsule in place until the balloon deflation mechanism is initiated.

As with the previous embodiments described, in addition to performing the function of controlling the heating elements, the combined microelectronic control and power supply 135 may communicate with the remote control 100 to confirm that the deflation mechanism has been activated. Following receipt of a confirmation signal, the physician and patient may then track the progress of the passing of the device.

To ensure the device of the present invention will pass easily, the intragastric balloon of the present invention may be constructed of a thin, highly acid-resistant shell material. In addition, the intragastric balloon may be shaped to encourage collapse into a bullet shape for smooth passage through the intestines. This shape may be created by pre-formed convolutions in the shell that would expand into a substantially spherical or ellipsoidal shape when inflated, but would retract into its small collapsed shape when the remote deflation mechanism was triggered.

The remote control may take the form of a handheld control unit that may feature an LCD display and/or similar type of display and a control panel, such as a keyboard or touchscreen, to operate the device. The remote control may feature a series of menus that allow an operator to program (or read/determine) the microelectronics to contain in memory important information such as the intragastric balloon's size, patient's name, implanting physician, and the date it was implanted. The remote control may communicate with the sensor via telemetry through radiowaves. The FDA and globally recognized communications band (WMTS 402-405 Mhz) may be used in some embodiments, and an authentication process (e.g., digital handshake signal, PIN verification, or other similar verification process) can be used to ensure that the device cannot be accidentally accessed or controlled by another control mechanism other than the remote control. The telemetry control signal can be sent from approximately a foot or possibly a greater distance from the patient and will typically not require the patient to disrobe to query the sensor or to change its parameters. The remote control is preferably able to read and write information to the microelectronics contained in the intragastric balloon. The remote control may also be password controlled to prevent unauthorized personnel from querying the device. The display of the remote control, which may include visual and audio outputs, typically will display or output the sensed parameter of the remote deflation valve's condition or physical parameter whether this parameter is "open", "closed", or any other physical parameter that the remote control is adjusted to monitor.

EXAMPLES

The following examples describe various procedures using the method and device of the present invention.

Example 1

Remote Deflation of an Intragastric Balloon Containing a Sealing Plug

In this example, the patient is an overweight male who has previously had an intragastric balloon inserted into his stomach. The intragastric balloon has been implanted for a full course of treatment for six months, and the surgeon is prepared to remove the balloon.

The removal of the balloon is performed in an outpatient setting at the doctor's office. Reference is made to FIGS. 2a and 2b for the remote deflation valve utilized in this example.

In order to open deflation valve 16, the physician activates the remote deflation mechanism from outside the body using a remote control 100, such as that depicted in FIG. 9. The physician holds remote control 100 near the stomach of the patient, and upon depression of a button, remote control 100 sends an activation signal through the patient's tissue to the microelectronic control 32.

Upon receiving the activation signal, microelectronic control 32 uses power from a battery 33 to begin increasing the temperature of heating element(s) 31. As the temperature of heating element(s) 31 begins to increase, the wax plug 30 begins to melt.

As the wax begins to melt, it collects on wicking surfaces 34. The collection of the wax on wicking surfaces 34 prevents the wax from clogging capillaries 35 and allows the fluid contained within intragastric balloon 10 to flow out of the balloon. Once the wax is melted and collected on wicking surfaces 34, capillaries 35 allow the free flow of the fluid contained inside the balloon through valve opening 36. In addition, once the wax is melted, the microelectronic control 32 sends a confirmation signal to the remote control 100, informing the doctor and patient that the deflation device has been activated.

Through the normal movements and contraction of the stomach walls, the balloon drains of the saline contained inside and shrinks down to a size that is passable through the human body. The microelectronics, heating elements, and battery are safely contained within the valve structure such that they do not present any danger to the patient.

Having received the confirmation signal, the patient may now leave the doctor's office and return home. The patient tracks the passage of the intragastric balloon and informs the doctor when it has passed.

Example 2

Remote Deflation of an Intragastric Balloon Containing a Separable Valve

In this example, the patient is an overweight female who has previously had an intragastric balloon implanted. After implantation the patient has experienced significant undesired side effects resulting from the implantation, including nausea, vomiting, and general abdominal discomfort. Therefore, the patient desires to have the remote deflation mechanism activated, thus allowing the balloon to be passed.

As with the first example, the balloon removal is performed in an outpatient setting at the doctor's office. Reference is made to FIGS. 8a and 8b for the remote deflation mechanism utilized in this example.

In order to cause the intragastric balloon 90 to deflate, the physician activates the remote deflation mechanism using a remote control 100, such as that depicted in FIG. 9. The physician positions remote control 100 near the stomach of the patient, and upon depression of a button, remote control 100 sends an activation signal through the tissue of the abdominal cavity to the microelectronic control 95.

Microelectronic control 95 has an antenna for receiving the activation signal from remote control 100. Upon receiving the activation signal, microelectronic control uses power from battery 96 to begin increasing the temperature of heating element(s) 93. As the temperature of heating element(s) 93 begins to increase, the temperature of cutting wire 94 also begins to increase. The increased temperature of the cutting wire causes the valve/balloon bond 92 to deteriorate, resulting in separation of the valve 91 from shell 97.

As the valve/balloon bond 92 breaks and separates from the shell, the normal movements of the stomach cause the fluid contained inside the balloon to freely flow through the opening 98. The normal movements and contraction of the stomach walls cause the intragastric balloon to completely drain of the fluid contained inside and shrink down to a size that is passable through the human body. The microelectronics, heating elements and battery are safely contained within the valve structure such that they do not present any danger to the patient. Because the entire intragastric balloon may now comprise two separate pieces, the passing of the balloon and valve is facilitated.

Once the valve/balloon bond has been broken, the microelectronic control 95 sends a confirmation signal to remote control 100 to confirm that the deflation mechanism has been activated. Following receipt of a confirmation signal by the remote control, the procedure is complete and the patient can return home and wait until the shell and valve assembly pass through the system. The patient tracks the passage of the intragastric balloon and informs the doctor when it has passed.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

Example 3

Remote Deflation of an Intragastric Balloon Containing a Valve Capsule

In this example, the patient is an overweight male who has previously had an intragastric balloon inserted into his stomach. The intragastric balloon has been implanted for a full course of treatment for six months, and the surgeon is prepared to remove the balloon.

The removal of the balloon is performed in an outpatient setting at the doctor's office. Reference is made to FIGS. 10*a* and 10*b* for the remote deflation valve utilized in this example.

In order to deflate balloon 109, the physician activates the remote deflation mechanism from outside the body using a remote control 100, such as that depicted in FIG. 9. The physician holds remote control 100 near the stomach of the patient, and upon depression of a button, remote control 100 sends an activation signal through the patient's tissue to the combined microelectronic control and power source 115.

Upon receiving the activation signal, the combined microelectronic control and power source 115 uses power to begin increasing the temperature of heating element(s) (not shown) that are connected to the torsional spring 113. As the temperature of the heating element(s) begin to increase, the temperature of shape memory torsional spring 113 also begins to increase, thereby causing the spring to deform and reduce in diameter. As the diameter decreases, the seal between valve capsule 111 and balloon collar 114 is broken. The valve capsule is separated from the shell, and fluid contained inside the balloon freely flows through the opening 116 (FIG. 10*b*) that is created by the separation of the two portions.

Through the normal movements and contraction of the stomach walls, the balloon drains of the saline contained inside and shrinks down to a size that is passable through the human body. The combined microelectronics control and power supply and heating element(s) are safely contained within the valve capsule such that they do not present any danger to the patient.

Having received the confirmation signal, the patient may now leave the doctor's office and return home. The patient tracks the passage of the intragastric balloon and informs the doctor when it has passed.

Any and all features described herein and combinations of such features are included within the scope of the present invention provided that the features of any such combination are not mutually inconsistent.

While this invention has been described with respect to various specific examples and embodiments, it is to be understood that the invention is not limited thereto and that it can be variously practiced within the scope of the following claims.

What is claimed is:

1. An intragastric balloon apparatus with a heat deformable element for facilitating weight loss in a patient, the apparatus comprising:
 a shell suitable for placement in a stomach of the patient and capable of being inflated with a fluid;
 a valve mechanism coupled to the shell and having
  a valve,
  a heat deformable element configured to deform upon application of an amount of heat sufficient to raise the temperature of the heat deformable element at least greater than an internal temperature of the stomach, and
  a plug for sealing the valve and detachably coupled to the heat deformable element, the plug configured to move from a sealed position to an unsealed position when operated on by the deforming heat deformable element; and
 a remote control device capable of sending a signal from outside the patient to the valve mechanism in order to effectuate deflation of the shell in vivo;
 wherein when the heat deformable element is heated and deforms, the plug is configured to be ejected and detached from the heat deformable element, thus allowing the balloon to drain.

2. The apparatus of claim 1 wherein the valve mechanism requires no implantable battery to move the plug from the sealed position to the unsealed position.

3. The apparatus of claim 1 wherein the valve mechanism is remotely powered by magnetic coupling from an external source.

4. The apparatus of claim 1 wherein the plug has an enlarged portion for blocking a flow of fluid from exiting the shell when the plug is in the sealed position.

5. The apparatus of claim 1 wherein the plug is configured to block capillaries in fluid communication with an interior of the shell when the plug is in the sealed position.

6. The apparatus of claim 1 wherein the valve mechanism is powered by a power source selected from a group consisting of (a) a battery, (b) a capacitor, (c) an induction coil, (d) a fuel cell, (e) body motion of the patient, (f) body chemistry of the patient, and (g) body temperature changes of the patient.

7. The apparatus of claim 1 wherein the release of the fluid from the shell cools the application of the amount of heat.

8. The apparatus of claim 1 wherein the shell is configured to collapse into a bullet shape upon deflation for smooth passage through the patient.

9. The apparatus of claim 8 wherein the bullet shape is produced by a preformed convolution in the shell.

10. A method for the in vivo remote deflation and removal from a patient of an intragastric balloon containing a volume of a fluid and a heat deformable element, the method comprising the steps of:
providing a fluid filled shell in a stomach of the patient;
providing a valve mechanism coupled to the shell and having a plug and a heat deformable element detachably coupled to the plug;
applying heat to the heat deformable element to deform the heat deformable element to thereby elect and detach the plug from the heat deformable element for moving the plug from a sealed configuration to an unsealed configuration to allow the fluid to exit the shell; and
allowing normal intragastric movements to facilitate release of the fluid from the shell and passing of the shell from the body.

11. The method of claim 10 further comprising the step of tracking the shell as it passes from the body.

12. An intragastric balloon apparatus for facilitating weight loss in a patient, the apparatus comprising:
a shell implantable in a stomach of the patient and inflatable with a fluid;
a valve mechanism coupled to the shell and having:
  i. a valve,
  ii. a heat deformable element configured to deform upon receiving an amount of heat sufficient to raise the temperature of the element above the temperature inside the stomach, and
  iii. a plug for selectively sealing and unsealing the valve and detachably coupled to the heat deformable element, the plug configured to move from a sealed position to an unsealed position when operated on by the deforming heat deformable element; and
a remote control device capable of sending a signal from outside the patient to the valve mechanism in order to apply at least enough heat to the heat deformable element to raise the temperature of the element above the temperature inside the stomach to deform the heat deformable element to thereby eject and detach the plug from the heat deformable element to move the plug from the sealed position to the unsealed position to effectuate sufficient deflation of the shell in vivo to allow removal of the shell.

13. The apparatus of claim 12, wherein the heat deformable element comprises a shape memory material.

14. The apparatus of claim 12, wherein the valve mechanism requires no implantable battery to move the plug from the sealed position to the unsealed position.

15. The apparatus of claim 12, wherein the valve mechanism is remotely powered by magnetic coupling from an external source.

* * * * *